Figure 1:
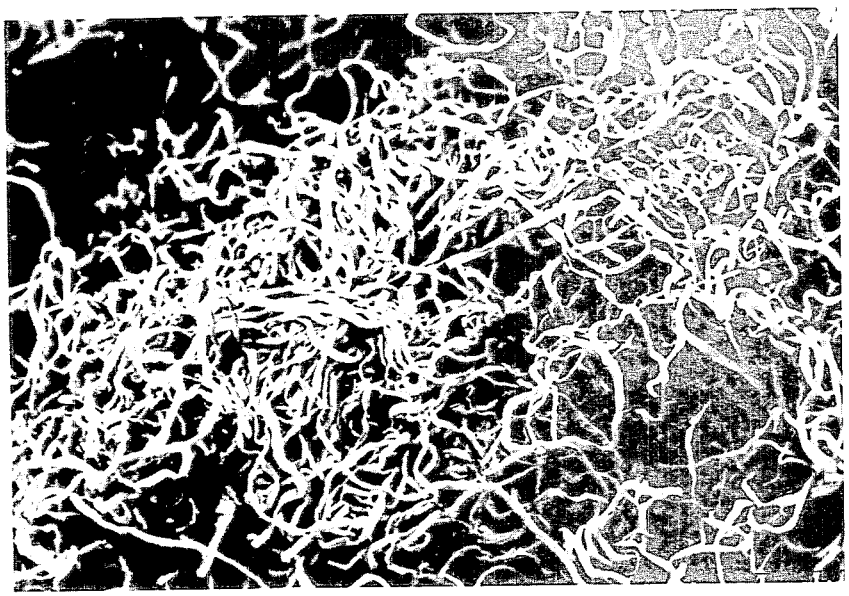

United States Patent [19]

Karlsson et al.

[11] 4,256,877
[45] Mar. 17, 1981

[54] METHOD OF MANUFACTURING CELLULOSE DERIVATIVE

[75] Inventors: Alf H. Karlsson, Njurunda; Hans E. Lundström, Alnö; Lars-Henrik Olsson, Njurunda, all of Sweden

[73] Assignee: SCA Development Aktiebolag, Sweden

[21] Appl. No.: 860,250

[22] Filed: Dec. 13, 1977

[30] Foreign Application Priority Data

Dec. 21, 1976 [SE] Sweden ................................ 7614342

[51] Int. Cl.³ ............................................. C08B 3/22
[52] U.S. Cl. ............................... 536/59; 106/193 R; 128/284; 162/111; 536/62; 536/87
[58] Field of Search ........................ 536/59, 62, 87; 162/111; 106/193 R

[56] References Cited

U.S. PATENT DOCUMENTS

| | | | |
|---|---|---|---|
| 962,505 | 6/1910 | Funke | 162/111 |
| 2,602,042 | 7/1952 | Abbott | 128/156 |
| 2,940,890 | 6/1960 | Braun | 162/111 |
| 3,005,456 | 10/1961 | Graham | 128/285 |
| 3,382,140 | 5/1968 | Henderson et al. | 162/111 |
| 3,525,735 | 8/1970 | Miller | 536/60 |
| 3,589,364 | 6/1971 | Dean et al. | 128/285 |
| 3,658,790 | 4/1972 | Bernardin | 536/62 |
| 3,691,154 | 9/1972 | Bernardin | 128/285 |
| 3,739,782 | 6/1973 | Bernardin | 536/62 |
| 3,804,092 | 4/1974 | Tunc | 536/59 |
| 3,821,068 | 6/1974 | Shaw | 162/111 |
| 3,919,385 | 11/1975 | Smith | 260/17 R |
| 3,997,647 | 12/1976 | Lassen | 106/177 |
| 4,084,591 | 4/1978 | Takebe et al. | 128/285 |

FOREIGN PATENT DOCUMENTS

| | | |
|---|---|---|
| 762553 | 7/1967 | Canada . |
| 581711 | 10/1946 | United Kingdom . |
| 820826 | 9/1959 | United Kingdom . |
| 1135936 | 12/1968 | United Kingdom . |
| 1391725 | 4/1975 | United Kingdom . |

Primary Examiner—Ronald W. Griffin
Attorney, Agent, or Firm—Lerner, David, Littenberg & Samuel

[57] ABSTRACT

An absorbent cellulose material is disclosed which comprises a substituted cellulose having an average degree of substitution sufficiently low to render the material insoluble and in which the fibers have an increased surface area formed by bursting the fibers during drying. In addition, a method of manufacturing such absorbent material is also disclosed which comprises providing an insoluble substituted cellulose material having an average degree of substitution sufficiently low to render the material insoluble, swelling the material to its maximum swelled state, fixing the material in that state, and drying the material while maintaining the material in its swelled state to thereby prevent shrinkage of the material during drying and to cause the fibers to burst during drying.

21 Claims, 6 Drawing Figures

METHOD OF MANUFACTURING CELLULOSE DERIVATIVE

The present invention relates to a method of manufacturing absorbent material out of cellulose derivatives, said absorbent material being especially intended for use in sanitary products such as sanitary napkins, tampons, facial napkins, diapers and the like.

Cellulose ethers are especially suitable cellulose derivatives, but other cellulose derivatives such as cellulose esters can also be used. Carboxymethyl cellulose (CMC), preferably its alkali or ammonium salts such as sodium carboxymethyl cellulose, can be mentioned as an example of cellulose ethers.

It is previously known to use carboxymethyl cellulose as absorption material in tampons for absorbing menstrual liquids. The carboxymethyl cellulose used herewith has been dried in a conventional manner in a drying drum without fixation of the material structure, and thereafter refined. The average substitution degree (DS) for this carboxymethyl cellulose, i.e. the number of carboxymethyl groups per anhydroglucose unit in the cellulose, has amounted to at most 0.35. However, this material has properties which are so similar to the properties of non-substituted material, that is, it has more or less the same low absorption capacity, that the cost of the substitution cannot be justified.

It is also previously known to use carboxymethyl cellulose having an average substitution degree greater than 0.35 for absorption purposes, said cellulose having been heat treated so that, according to information provided, it has become insoluble in water. The heat treatment is effected so that the material is heated in an oven under pressure at a temperature of 120°–170° C. for a period of 1–20 hours, and thus the CMC is subjected to cross-linking conditions. Some CMC-derivatives have been manufactured in this manner and have relatively good absorption. However, with this method, the absorption capacity and speed properties will become dependent upon each other to some extent so that a material having high adsorption capacity will have a lower absorption speed and vice versa. The relatively high manufacturing costs can also be noted as a further disadvantage.

Great liquid-retaining ability and rapid absorption, but also high cost, is obtained when the absorption material is manufactured according to U.S. Pat. No. 3,589,364 by means of wet CMC having an average substitution degree of 0.4–1.6 being cross-linked with epichlorohydrin to a water-insoluble product.

According to U.S. Pat. No. 3,919,385, an absorbent material is manufactured by means of mixing a "cyanoethylated viscose" and an aqueous solution of polyvinyl pyrrolidon with a non-substituted filament-forming viscose constituting the major portion of the mixture. This mixture is converted into fibres consisting of non-substituted regenerated cellulose in which regenerated cyanoethylene cellulose and polyvinyl pyrrolidon are homogenously distributed.

Swedish patent application No. 7,507,172 describes a method of drying a modified cellulose-containing material in which the product is first brought to maximum swelling by means of washing with water, after which it is acidified to a pH which reduces the swelling to a minimum. The product is then converted to salt form under non-swelling solvent conditions and dried in an oven by means of evaporation of the solvent.

According to Swedish Lay Open Print No. 305,714, it is difficult or impossible to treat etherized cellulose products having a substitution degree of 0.1–0.7 in the swelled state. Furthermore, it is claimed that drying by means of heat usually leads to the formation of hornlike hard material which is hardly suitable as absorbent material. This is a technical prejudice to the extent that said difficulty can be easily overcome by means of using the present invention as described in more detail below. The purpose of the present invention is to achieve a method of manufacturing absorbent material out of cellulose derivatives, preferably carboxymethyl cellulose, having the greatest possible absorption capacity.

Another purpose of the present invention is to achieve as economical a manufacturing process as possible, that is, a process which results in as low a cost as possible for the final product.

Another purpose of the invention is to make possible the use of available plants in drying the absorbent material.

The product according to the invention is characterized in that it contains cellulose derivatives such as cellulose ethers, for example, carboxymethyl cellulose, carboxyethylene cellulose, carboxymethylhydroxyethylene cellulose, hydroxyethylene cellulose, hydroxypropylene cellulose or methyl cellulose, or cellulose esters, for example, cellulose sulphate or cellulose phosphate, in fibre form, having an average substitution degree (DS) of at most 0.40, in which the fibres have burst during drying so that their surfaces have been enlarged considerably.

According to the invention, this is achieved by means of a cellulose derivative such as a cellulose ether, for example, carboxymethyl cellulose, carboxyethylene cellulose, carboxymethylhydroxyethylene cellulose, hydroxyethylene cellulose, hydroxypropylene cellulose or methyl cellulose, or a cellulose ester, for example, cellulose sulphate or cellulose phosphate in fibre form and having an average substitution degree (DS) of at most 0.40, being brought to the swelled state, fixed in said state, and thereafter dried, the substantial portion of the swelling agent being removed while the swelled material structure is maintained and shrinkage is prevented.

The invention can be carried out with the help of one or more steam-heated drying rollers upon which the cellulose material is fixed in a roller nip between the rollers or between a supply roller and the drying roller, a coating nozzle being movable reciprocally along the drying roller or drying rollers so that the cellulose material, which has the form of a paste, shall be distributed relatively evenly over the roller nip, and a doctor blade for removal of the mat which is formed during fixing and drying on the roller, said doctor blade being adjustable to provide the removed web with a creped structure.

During cooking, the crystalline structure of the cellulose is affected, and the crystallinity can also be affected by substitution. By means of selecting a suitable substituent, for example, carboxymethyl groups, a steric effect is obtained, said effect effectively preventing the normal intermolecular bonding between the glucose units. The carboxymethyl groups function as spacers between the fibers and a so called balloon effect is obtained. Said effect consists of swellings arising between the areas where the crystalline fibre structure remains. The steric effect is reinforced further by means of the hydrophilic properties of the CM-group. The hydrophilic advantages of the CMC can then be put to practical use by means of maximum fibre swelling of the CMC followed by the removal of the swelling agent in such a manner that the normal configuration cannot be rebuilt.

In mixtures of highly-substituted CMC, the absorption takes place very slowly or ceases entirely due to the fact that the carboxymethyl cellulose swells so heavily at its surface that further transportation of liquid through the material is prevented. This is the so called stop layer effect. The CMC material must be lowly substituted in order that a good absorption result shall be obtained.

CMC having a low substitution degree has attracted rather slight interest in the literature, and in some cases it has only attracted interest in connection with the manufacture of CMC sheets. However, it has now unexpectedly been shown that an optimum absorption capacity can be obtained for CMC having an average substitution degree of up to 0.40, preferably up to 0.30, and a DS of 0.24 has been found to be especially suitable. However, the substitution degree shall be adjusted so that the fibre structure is maintained while the pulp still remains insoluble.

In order to achieve a material having maximum absorption capacity, carboxymethyl cellulose was manufactured having varying substitution degrees (DS) based on different pulps. It was found that CMC from birch sulphate cellulose becomes soluble at a lower DS while CMC from bleached pine sulphate cellulose becomes soluble at a DS of approximately 0.40. Good results have been obtained in the manufacture of CMC from viscose pulp and bleached pine sulphate cellulose.

After the CMC quality in question has been manufactured, it is dried in such a manner that maximum absorption capacity is obtained.

For many years now, drying on heated rollers has been used in the production of soluble carboxymethyl cellulose, wallpaper glue and the like; c.f. Swedish Pat. No. 147,713. According to this patent specification, pulp is deposited as a thin film on rollers having a temperature of approx. 150° C. The film is dried to brittleness, and is then refined to flakes. Despite the fact that this is a method which has been used for a long time, it has never been used to dry insoluble CMC due to the fact that it has been considered impossible to obtain absorbent material by means of drying in heat. This has been expressed in the above-mentioned Swedish Lay Open Print No. 305,714. To date, a horn-like hard material which has not been able to be used as absorbent material has been obtained by drying in heat.

The manufactured CMC material shall then be dried so that maximum absorption capacity is obtained. This can preferably take place in two different manners, namely freezedrying and roller drying. As is described in more detail below, the material is first brought to its maximum swelled state. According to the invention, this state is maintained during drying by means of the fibre being fixed, and the desired high absorption capacity can be achieved thereby. Freeze drying has primarily been used within the foodstuffs industry and is effected in a vacuum at a temperature below 0° C. This process is used for drying of carboxymethyl cellulose so that the material is frozen and then dried by means of the water being removed in vapour form directly from its solid ice phase. At the present time, this is a rather uneconomical method which, however, can even at the present time be justified by means of the material being obtained in a very advantageous form, namely as granules having very good absorption properties, thanks to the fibres being dried while they are fixed in a swelled state by means of the freezing. These granules can then be further refined as desired.

As regards roller drying, it has now surprisingly been found that if one is able to make the material fasten onto a drying roller, this is sufficient in order to fix the material and conserve its structure so that drying takes place without any shrinkage.

In a normal drying of fibres, the water inside the walls of the fibres is removed, and the fibres shrivel up. By means of fixing the fibres according to the invention, for example, by means of freezing or on a drying roller, the fibre is mechanically prevented from shrivelling, and the fibre bursts instead when the mechanical forces become sufficiently great. The bursting takes place in such a manner that the fibres burst open along one line or major break and, in so doing, the surface of the burst fibre which is available for water absorption becomes several times greater than in a fibre dried in the normal manner without swelling and bursting.

According to a preferred embodiment, the pulp is then diluted with water to a dry content of approx. 10% and kneaded into a paste which is pumped to the drying roller or drying rollers by means of a special pump. The drying arrangement can be designed to have two drying rollers which form a roller nip, or as one drying roller and a supply roller abutting said drying roller and forming a roller nip. The paste is so viscous that distribution over the roller should suitably be effected by means of the paste being supplied by means of a nozzle which moves reciprocally back and forth along the roller.

When the paste is distributed over the drying roller or drying rollers, a fixation of a film on the drying roller takes place in the roller nip and the thickness of this film is regulated by means of setting the distance between the rollers in the nip. After about three fourths of a turn of the drying roller, the film has, by means of the loss of water, converted into a mat which is scraped off of the roller by means of a doctor blade. The mat can herewith be provided with a creped appearance. The dry content of the paste is of importance, but is not critical. In the event of exceedingly high dry content, a hard, parchment-like material having very poor absorbency is formed, and in the event of exceedingly high dry content, the amount of water which is to be evaporated will become excessively great. A hard, parchment-like material can also arise if the temperature of the drying roller is too high or if the roller nip is too narrow due to the evaporation prior to the material passing through the roller nip then taking place so rapidly that the dry content becomes too great. If the dry content is too low, it can be difficult to get the material to attach itself to the rollers because a steam layer will be formed between the rollers and the material. This is called Leidenfrost's phenomenom.

The results obtained by means of drying according to the invention show that a marked increase of the absorption capacity is obtained as compared to conventionally dried material, said increased absorption capacity being fully comparable to that which is obtained by means of freeze drying.

Figure 3:
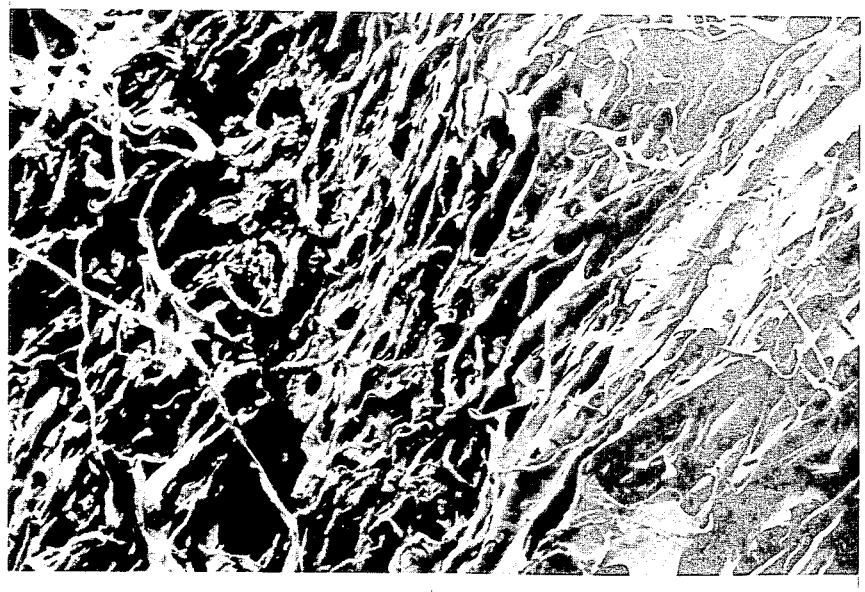
Figure 4:
Figure 5:
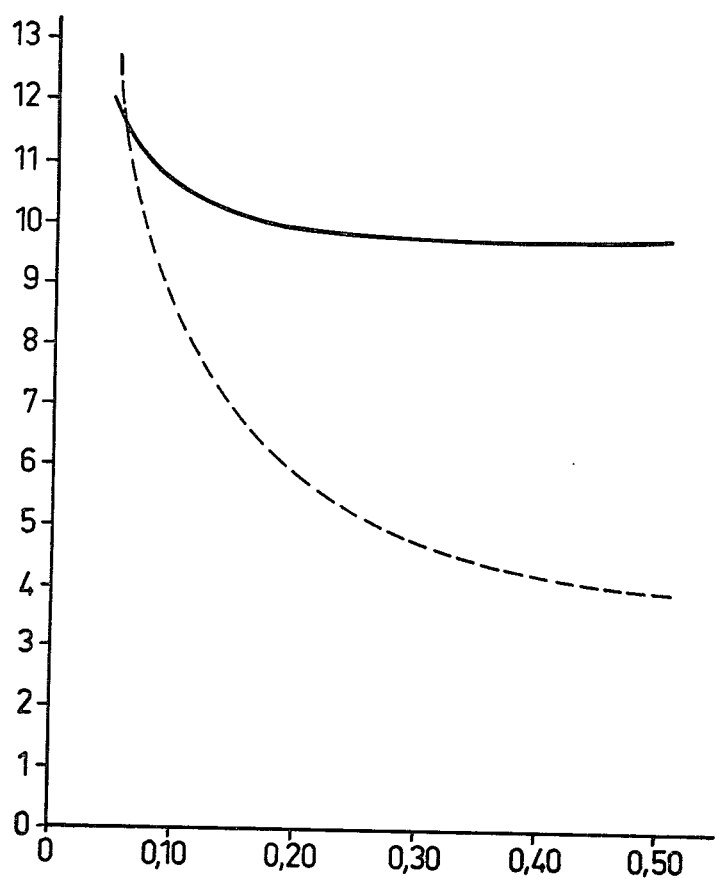
Figure 6:
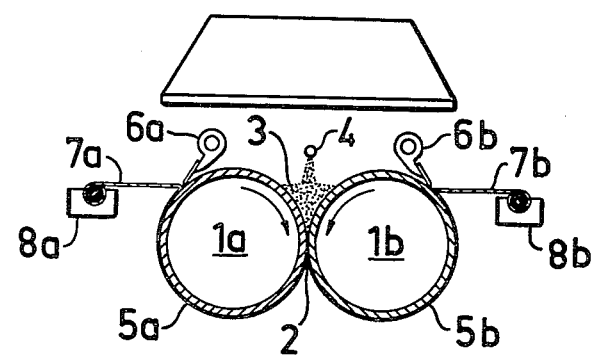

The invention shall be described in more detail in connection with the accompanying drawings, FIGS. 1, 2, 3 and 4 of which show electron microphotographs of conventionally dried CMC compared to CMC dried according to the invention, FIG. 5 showing absorption curves for CMC dried according to the invention and dried conventionally, and FIG. 6 showing a drying roller for drying CMC according to the invention.

In order to further illuminate the differences and explain why an improved absorption capacity can be obtained with CMC material dried according to the invention, a morphological investigation has been carried out by means of electron microscoping.

The samples were prepared by STFI by means of a special technique which is based on coating the material in a high vacuum with metallic gold to a thickness of approx. 500 Å. The pictures shown in FIGS. 1–4 are prints of photographs taken in STFI's scanner electron microscope, Cambridge Stereoscan 600.

Figure 2:

FIG. 1 shows conventionally dried CMC having a DS of 0.25 from a viscose pulp enlarged 50 times. FIG. 2 shows the same fibre enlarged 200 times. FIG. 3 shows CMC fibre having a DS of 0.25 from viscose pulp which has been swelled and roller dried enlarged 50 times, and FIG. 4 shows the same fibre enlarged 200 times.

As can be seen in the figures, the greatest difference lies in the marked increase of the size of the fibre surface and the accompanying increase in absorption capacity. The fibre structure is essentially totally split open which should be due to the fact that, during drying, the fibres burst open because of their not being able to move or shrink due to fixation. The surfaces of the fibres which have been roller dried after swelling according to the invention are, as can be seen, several times greater than the surfaces of the fibres of conventionally dried CMC.

When the absorption material according to the invention is manufactured by means of swelling followed by roller drying, it is obtained in the form of a paper-like web which, preferably, can be provided with a creped structure for increased softness and elasticity which is important for product and production adaptation. The material can be used as the sole absorption material for absorping of body liquids in different sanitary, hygienic or hospital products, but can also be advantageously combined with traditional absorption material such as cellulose wadding and defibrated pulp, chemical or mechanical or mixtures thereof.

No matter whether the material is used in sheet or defibrated form, it is suitably placed in a separate layer. In the defibrated state, it can also be mixed in arbitrary proportions with other organic or inorganic absorption material in order to increase their liquid-retaining ability. The combination with other possible absorbent material can also be effected prior to the above-described drying process.

The reason for the great freedom of selection of applications is that the novel absorption material does not give rise to stop layer effects. Rather, it cooperates with surrounding material by means of its both absorbing liquid from the same and distributing the liquid within itself.

One type of testing method suitable to use on this group of material where capillary absorption has been totally or partially replaced by swelling absorption is called "demand wettability," that is, the liquid absorption is totally regulated by the material and possible stop effects result in slow or very low absorption even if the test time is extended. One testing method which can be easily adapted to the material and product preconditions in question is SIS 251,228.

In the present case, a press tool providing very good reproducability even when the the material expands heavily in the lateral direction when liquid is absorbed can be used. The press tool consists of a ring which provides a surface of 25 cm$^2$ and which rests against a removable bottom plate. The bottom plate has different heights so that different densities can be obtained during compression by means of a press body in a jack, for example, 0.3, 0.4, 0.5 and 0.6 g/cm$^3$.

The sample bodies were then placed in a cylinder which prevents lateral expansion and is loaded with a weight. By means of a hole in the bottom of the cylinder, the sample is in contact with the liquid which is to be absorbed by means of a hose. This hose or tube is connected to a burette which is designed so that the pressure from the liquid through the hose is exactly compensated by the weight placed on the sample in the cylinder so that only the absorption tendency of the sample causes the liquid to be absorbed. The hydrostatic pressure is 0. As soon as the sample is saturated, the transportation of liquid ceases. The amount of absorbed liquid can then be read on the burette. The absorption speed can also be determined with this apparatus.

With 1% NaCl-solution as sampling liquid, this type of testing method also provides a realistic understanding of what an absorption material is actually capable of absorbing when it comes to different body liquids. As most absorption products are subjected to load when they are used or, as tampons, are already compressed when they are initially used, the tests have been carried out at different density levels.

FIG. 5 presents a comparison, in diagram form, between a currently common absorption material, defibrated sulphate pulp or fluffed pulp, and the absorption material according to the invention. As no stop effects have been observed neither when the absorption material was used as sole component nor in a mixture with other material in the tests described here, the diagram only presents total absorption for the material according to the invention.

The curves reveal that while the absorption capacity for conventional material decreases heavily with incresing density, the absorption capacity for the material according to the invention is practically speaking independent of density.

The vertical distance between the drawn curves for a given density shows the gain which is obtained when the absorption material according to the invention is used.

FIG. 6 shows a preferred device for drying the material according to the invention. The device consists of two steam-heated drying rollers 1a and 1b which, together, form a roller nip 2. The paste-like material 3 is supplied to the roller nip 2 by means of a coating nozzle 4. The coating nozzle 4 can be moved reciprocally back and forth along the rollers and evenly distributes the material along the roller nip 2. The material 3 is fixed in the roller nip 2 to a film 5a and 5b respectively on the rollers 1a and 1b respectively. The film thickness can be varied by means of regulating the width of the roller nip. After the rollers have been moved three fourths of a turn, the now mat-like material is scraped off with the help of doctor blades 6a and 6b which can be controlled so that the material receives a creped structure. The material webs 7a and 7b can then be rolled up by means of rolling up devices 8a and 8b.

The following is an example of how the CMC starting material can be manufactured. This material is used in the subsequent examples.

10 kilos of "dry" pulp having a dry content of 94% was added to an SCA-Fs 160 1. Drais mixer during simultaneous spraying of 24% soda liquor and 5 kilos 96% ethanol for a period of 20 minutes. The temperature was maintained at 20° C. by means of a supply of cold water in an outer casing. The rapid knife defibrator of the mixer was run continuously.

One hour after start, 2,95 kg monochloroacetic acid, 0,5 mol/mol cellulose, dissolved in 5 kg 96% ethanol was added under cooling for a period of 10 minutes. The material was cooled for 20 minutes. Heating to 60° C. was initiated, which took 0.5 hours simultaneously as the knife defibrator was switched to intermittent operation at 1 minute's operation every ten minutes. The reaction was continued for 2 hours. The mixture was cooled and neutralized with 3.8 liters hydrochloric acid dissolved in 50 liters 30% ethanol. The material was thereafter washed with ethanol and/or water.

The invention will be described in more detail below by means of embodiments and with reference being made to the test results in the table below.

EXAMPLE 1

The CMC which is still alcohol wet and has a dry content of approx. 30% taken directly from manufacture is diluted with water to a dry content of 10%. Warm water is used to expediate the treatment. By means of kneading in a Nautamixer, a thick, viscous paste is obtained after about 15 minutes. Said paste could be transported further by means of a special pump.

Said paste, which consisted of the sodium salt of carboxymethyl cellulose in fibre form and having a DS of 0.24 was mixed with water having a temperature of 100° C. so that a uniform slurry having a dry content of 4% was obtained. This slurry was frozen and dried at a pressure of 1.33 Pa ($10^{-2}$ mmHg).

EXAMPLE 2

Carried out in the same manner as example 1, but having a slurry dry content of approx. 10%.

EXAMPLE 3

Carried out in the same manner as claim 1, but the product was freeze-dried at a maximum temperature of 60° C. of the dry material at a pressure of approx. 276 Pa (approx. 2 mmHg).

EXAMPLE 4

Carried out according to example 2, but at a dry material maximum temperature of 80° C.

EXAMPLE 5

The paste having a dry content of approx. 10% was frozen in the form of floe which was granulated and freeze-dried according to any of examples 2 or 3.

EXAMPLE 6

Sodium carboxyrethyl cellulose having a DS of 0.24 was kneaded with water to a dry content of approx. 10% and dried according to any of examples 1-4.

EXAMPLE 7

Sodium carboxymethyl cellulose having a DS of 0.24 was kneaded with water to a dry content of approx. 10% and roller dried according to the preferred embodiment, c.f. pages 5 and 6, at a temperature of 140° C.

EXAMPLE 8

Carried out according to example 7, but roller dried at 175° C.

EXAMPLE 9

Socium carboxymethyl cellulose having a DS of 0.28 was treated according to any of examples 1-7.

EXAMPLE 10

Sodium carboxymethyl cellulose having a DS of 0.19 was treated according to any of examples 1-7.

EXAMPLE 11

Sodium hydroxyethylene cellulose having a DS of 0.24 was kneaded in the same manner as sodium carboxymethyl cellulose according to example 1 and was roller dried according to example 7.

EXAMPLE 12

The invention was tested on cellulose sulphate in the same manner as example 11.

TABLE

Absorption capacities of low etherized and swelled CMC derivative of 1% NaCl in water at a load of 15 g/cm$^2$ and a hydrostatic pressure of 0. Density 0.5 g/cm$^3$.

| Example | CMC | Absorption ml/g | Remarks |
|---|---|---|---|
| A | 0.24 | 6.3 | Untreated sample |
| 1 | 0.24 | 11.1 | |
| 2 | 0.24 | 11.0 | |
| 3 | 0.24 | 10.2 | |
| 4 | 0.24 | 11.5 | |
| 5 | 0.24 | 12.0 | |
| 6 | 0.24 | 11.5 | |
| 7 | 0.24 | 10.7 | |
| 8 | 0.24 | 11.0 | |
| 9 | 0.24 | 12.0 | |
| 10 | 0.19 | 11.2 | |
| 11 | 0.24 | 11.0 | |
| 12 | 0.24 | 11.0 | |

The table reveals that very good absorption capacities are obtained for the materials manufactured by means of the method according to the invention, and that the invention can also be used for other cellulose derivatives having properties similar to carboxymethyl cellulose, such as carboxyethylene cellulose, carboxymethylhydroxyethylene cellulose, hydroxyethylene cellulose, hydroxypropylene cellulose or methyl cellulose, or cellulose esters, for example, cellulose sulphate or cellulose phosphate.

We claim:

1. An absorbent cellulose material, comprising a substituted cellulose material having an average degree of substitution sufficiently low to render said material insoluble in water, said material comprising fibers having an increased surface area formed by swelling said material, fixing said material in said swelled state, and drying said material while maintaining said material in said swelled state, thereby bursting said fibers during drying.

2. An absorbent cellulose material according to claim 1, wherein said material has an average degree of substitution of less than 0.40.

3. An absorbent cellulose material according to claim 1 wherein said cellulose material is selected from the group comprising carboxymethyl cellulose, carboxyethylene cellulose, carboxymethylhydroxyethylene cellulose, hydroxyethylene cellulose, hydroxypropylene cellulose, methyl cellulose, cellulose sulphate, cellulose phosphate, and mixtures thereof.

4. The absorbent cellulose material of claim 1 wherein said material is combined with additional absorbent material.

5. The absorbent cellulose material of claim 4 wherein said additional material is selected from the group consisting of cellulose wadding, chemical defibrated pulp, mechanical defibrated pulp, thermomechanical pulp, bentonite, and mixtures thereof.

6. An absorbent cellulose material, comprising a substituted cellulose material having an average degree of substitution of at most 0.40, said material comprising fibers having an increased surface area formed by swelling said material, fixing said material in said swelled state, and drying said material while maintaining said material in said swelled state, thereby bursting said fibers during drying.

7. A method of manufacturing absorbent cellulose material comprising, providing a substituted cellulose material having an average degree of substitution sufficiently low to render said material insoluble in water, swelling said material to its maximum swelled state, fixing said material in said swelled state, and drying said material while maintaining said material in said swelled state, thereby preventing shrinkage of said material during drying and causing the fibers of said material to burst during drying.

8. The method of claim 7 wherein the average degree of substitution of said material is less than 0.40.

9. The method of claim 7 wherein said material is fixed by freezing said material and said material is dried by freeze drying.

10. The method of claim 7 wherein said material is fixed by applying said material to a heating roller in the form of a paste and said material is dried by applying heat to said roller.

11. The method of claim 7 wherein said cellulose material is selected from the group comprising carboxymethyl cellulose, carboxyethylene cellulose, carboxymethylhydroxyethylene cellulose, hydroxyethylene cellulose, hydroxypropylene cellulose, methyl cellulose, cellulose sulphate, cellulose phosphate, and mixtures thereof.

12. The method of claim 11 wherein said cellulose material is carboxymethyl cellulose.

13. The method of claim 7 wherein the average degree of substitution of said material is less than 0.30.

14. The method of claim 7 wherein the average substitution degree of said material is less than 0.24.

15. The method of claim 7, further comprising the step of defibrating said material subsequent to drying.

16. The method of claim 7 wherein said material is combined with additional absorbent material subsequent to drying.

17. The method of claim 16 wherein said additional material is selected from the group consisting of cellulose wadding, chemical defibrated pulp, mechanical defibrated pulp, thermomechanical pulp, bentonite, and mixtures thereof.

18. The method of claim 7 wherein said material is combined with additional absorbent material prior to drying.

19. The method of claim 18 wherein said additional material is selected from the group consisting of cellulose wadding, chemical defibrated pulp, mechanical defibrated pulp, thermomechanical pulp, bentonite, and mixtures thereof.

20. The method of claim 7 wherein said material is provided with a creped surface subsequent to drying.

21. A method of manufacturing an absorbent cellulose material for use in sanitary products containing a water-insoluble cellulose derivative, which method comprises mechanically working a water-insoluble cellulose ether or a cellulose ester having an average degree of substitution of at most 0.40 in fiber form with water so as to achieve maximum swelling of the separate fibers, whereby a material in the form of a paste having approximately 10% dry content is obtained, supplying the paste to a roller nip between rollers heated by steam at a pressure of from 3.5 to 10 bars so that a film containing material in a swollen state is formed, the said film being fixed to the roller so that the separate fibers of the material are maintained in their mutual relationship which was achieved during the swelling, rapidly removing a substantial portion of the water in the paste so that the fibers burst whereby when the film is fixed onto the roller shrinkage of the material is avoided, and then removing the material which has been dried in this manner from the roller in the form of a continuous mat by means of a doctor blade, the said mat being capable of being provided with a creped surface.

* * * * *

UNITED STATES PATENT AND TRADEMARK OFFICE
CERTIFICATE OF CORRECTION

PATENT NO. : 4,256,877
DATED : March 17, 1981
INVENTOR(S) : Alf H. Karlsson et al It is certified that error appears in the above-identified patent and that said Letters Patent are hereby corrected as shown below:

Column 7, line 49, "276" should read --267--.

Signed and Sealed this

Twenty-third Day of June 1981

[SEAL]

Attest:

RENE D. TEGTMEYER

Attesting Officer      Acting Commissioner of Patents and Trademarks